United States Patent
Malinouskas et al.

[11] Patent Number: 5,882,300
[45] Date of Patent: Mar. 16, 1999

[54] WIRELESS PATIENT MONITORING APPARATUS USING INDUCTIVE COUPLING

[75] Inventors: Donald Malinouskas, Monroe; George Hojaiban, Meriden, both of Conn.

[73] Assignee: SpaceLabs Medical, Inc., Redmond, Wash.

[21] Appl. No.: 745,020

[22] Filed: Nov. 7, 1996

[51] Int. Cl.[6] .............................. A61B 5/00; A61B 8/00
[52] U.S. Cl. .................. 600/300; 600/453; 600/588; 600/591; 128/903
[58] Field of Search ......................... 128/903; 600/511, 600/546, 453, 588, 591

[56] References Cited

U.S. PATENT DOCUMENTS

| | | | |
|---|---|---|---|
| 3,638,642 | 2/1972 | Heflin, Sr. et al. | 340/870.15 X |
| 3,921,621 | 11/1975 | Baessler | 73/342 |
| 3,949,388 | 4/1976 | Fuller | 128/903 X |
| 4,109,644 | 8/1978 | Kojima | 600/437 |
| 4,186,749 | 2/1980 | Fryer | 128/903 X |
| 4,198,987 | 4/1980 | Cain et al. | 600/457 |
| 4,373,527 | 2/1983 | Fischell | 128/903 X |
| 4,573,475 | 3/1986 | Dukes et al. | 128/903 X |
| 5,143,171 | 8/1995 | Harrison et al. | 600/8 |
| 5,373,852 | 12/1994 | Harrison et al. | 600/546 |
| 5,511,553 | 4/1996 | Segalowitz | |
| 5,549,113 | 8/1996 | Halleck et al. | 128/903 |

OTHER PUBLICATIONS

IM77 Intrapartum Fetal Monitor, Advanced Medical Systems Brochure, May 1995.

Primary Examiner—Francis J. Jaworski
Attorney, Agent, or Firm—Seed and Berry LLP

[57] ABSTRACT

A wireless patient monitoring apparatus uses low frequency inductive coupling to couple signals from a transducer to monitoring and analysis instrumentation. Signals indicative of physiological functions are modulated onto a low frequency carrier and output from a self-contained portable transducer assembly via a transducer coil. A corresponding receiver coil receives the signals by electromagnetic induction. The received signals are demodulated and processed by instrumentation coupled to the receiver coil. A mattress pad containing the receiver coil is also disclosed. In a fetal monitor implementation, both wireless ultrasound and tocodynamometer transducers are provided.

27 Claims, 8 Drawing Sheets

WIRELESS PATIENT MONITORING APPARATUS USING INDUCTIVE COUPLING

BACKGROUND OF THE INVENTION

The present invention relates to patient monitoring apparatus such as fetal monitoring apparatus, and more particularly to a novel wireless patient monitoring apparatus that uses low frequency inductive coupling.

Apparatus for the real-time monitoring of physiological conditions in medical patients is well known. Examples of such apparatus include electrocardiogram recorders, heart rate monitors, electroencephalograph apparatus, maternal uterine activity monitors, and various other noninvasive medical instrumentation. Technology for monitoring such physiological functions includes ultrasound and tocodynamometer (TOCO) transducers. One type of instrumentation that benefits from the use of both ultrasound and tocodynamometer transducers is a fetal monitor, such as the Model IM77 Intrapartum Fetal Monitor manufactured by Advanced Medical Systems, Inc. of Hamden, Conn., U.S.A. This fetal monitor measures and records maternal and fetal activity during pregnancy through labor and delivery. Data on the fetal heart rate (FHR) and uterine activity (UA) is displayed on a front panel and simultaneously recorded on a trace (strip chart) recorder. FHR can be measured externally using Doppler ultrasound. Uterine activity can be measured externally using a TOCO transducer that incorporates, e.g., a strain gauge.

A disadvantage with prior patient monitoring systems, such as fetal monitors, is that the various transducers used to detect physiological functions required electrical cables in order to communicate the transducer signals to a console containing the user interface, analysis circuitry and output devices (e.g., strip chart recorder) used by medical professionals. Often, such cables become tangled, interfere with other medical procedures, and typically get in the way of the patient wearing them. Moreover, the need to be connected by cables limits the mobility of the patient and can cause discomfort. Additionally, wired transducers which are connected to a console that contains potentially dangerous electrical currents are not able to be used in underwater deliveries, due to safety concerns.

Past attempts to overcome the problems inherent with cabled transducers have focused on using telemetry (i.e., radio frequency signals) to provide wireless transducers. Although RF telemetry is advantageous in certain respects (such as a long range of operation which facilitates patient mobility), it also has various disadvantages in certain applications. For example, where different patients are being monitored in the same hospital, each monitor will have to operate at a different frequency to avoid conflict. Telemetry is also relatively costly to implement due to various transmitter and receiver requirements and the fact that government approval (e.g., by the Federal Communications Commission—FCC) is typically required. Telemetry fetal monitoring systems are also not well suited to underwater deliveries.

It would be advantageous to provide a wireless patient monitoring system that avoids the disadvantages of cabled transducers as well as the disadvantages of prior art telemetry systems. Such apparatus should be compact (a particular advantage for use with fetal monitors to be used in underwater deliveries) easy to use, and reliable.

The present invention provides a wireless patient monitoring system enjoying the aforementioned and other advantages.

SUMMARY OF THE INVENTION

In accordance with the present invention, wireless patient monitoring apparatus is provided, in which a transducer detects a physiological function. The transducer provides an output signal indicative of the physiological function. A modulator is provided for modulating a low frequency carrier (e.g., below about 9,000 hertz) by the transducer output signal. A transducer coil is associated with the modulator for coupling the modulated low frequency carrier to a corresponding receiver coil by electromagnetic induction. A monitoring circuit is coupled to receive the modulated low frequency carrier from the receiver coil. The transducer is designed for placement adjacent to a region of a patient to be monitored and provides the output signal to the monitoring circuit when the patient is in proximity to the receiver coil.

In an illustrated embodiment, the transducer, modulator and transducer coil are all situated in a common transducer housing. A power supply is provided in the housing for powering the transducer, modulator and associated circuitry situated in the housing. A motion sensor situated in the housing detects movement of the housing. The power supply is responsive to the motion sensor for providing power when the housing is moved. A keep-alive circuit can be provided for actuating the power supply to continue to provide power when the physiological function is being detected. In this manner, battery power is conserved when the unit is not in use.

Preferably, the housing is a waterproof housing. When the patient monitoring apparatus comprises a fetal monitor, a waterproof housing is particularly useful for underwater births.

The receiver coil can be situated in a mattress pad. The mattress pad is conveniently located under a patient who is lying in bed, either on top of or under bed sheets placed on the mattress. The receiver coil of the mattress pad will receive signals from the transducer coil via electromagnetic induction. A plurality of receiver coils can be provided in different planes of the mattress pad to enable clear reception of the transducer signal as the patient moves to different positions on the bed. Alternatively, or in addition, a plurality of transducer coils may be provided in different planes.

In an embodiment where the patient monitoring apparatus is a fetal monitor, the transducer can comprise an ultrasound transducer adapted to be placed on a mother's abdomen to measure fetal heart rate. Alternatively, or in addition to the ultrasound transducer, a tocodynamometer transducer may be provided. The TOCO transducer is placed on the mother's abdomen for providing a TOCO output signal indicative of uterine activity. The TOCO transducer comprises a TOCO modulator for modulating a low frequency TOCO carrier by the TOCO output signal. A TOCO transducer coil associated with the TOCO modulator couples the modulated low frequency TOCO carrier to the receiver coil by electromagnetic induction. The TOCO transducer is adapted to provide the TOCO output signal to a monitoring circuit via the TOCO transducer coil and the receiver coil when the mother is in proximity to the receiver coil.

In an embodiment where both ultrasound and tocodynamometer transducers are used, the output signals from each can be modulated on a separate subcarrier for inductive coupling to the receiver coil. For example, the TOCO transducer output signal may be FM modulated on a 3100 hertz carrier, and the ultrasound output signal may be FM modulated on a 8000 hertz carrier.

A battery operated power supply can be used to power the ultrasound and tocodynamometer transducers, together with their associated modulators and other circuitry. A first charging coil can be provided in each transducer housing for use in inductively charging the batteries. A receptacle is provided in a console portion of the patient monitoring apparatus for removably receiving the transducer housing. A second charging coil, located adjacent the receptacle, inductively provides a charging current to the first charging coil when the transducer housing is placed in the receptacle. Means are provided for communicating a low battery signal to an external alarm via the transducer and receiver coils. For example, a low battery signal can be modulated on the low frequency carrier together with the transducer output signal. When the monitoring circuit detects the low battery signal, it can actuate a signal to alert medical personnel to change the batteries in the transducer housing. Alternatively, a low battery condition can be signaled by slightly shifting the frequency of the carrier.

A mattress pad is provided for use with a wireless patient monitoring system. The mattress pad includes a planar flexible substrate having a length and width adapted to fit on a mattress. A wire coil has first and second terminal ends and is constructed and arranged to inductively receive a modulated low frequency signal carrying physiological information from a counterpart coil of a physiological function detector. A channel (e.g., trough) is provided in the substrate for enclosing the wire coil. A cable, having first and second conductors at a first end thereof, is connected to first and second terminal ends of the wire coil. A connector is connected to a second end of the cable for coupling the modulated low frequency signal to a patient monitor. The coil is preferably free to move within the channel in the mattress pad. In an illustrated embodiment, the channel runs along a perimeter of the mattress pad.

DETAILED DESCRIPTION OF THE INVENTION

Figure 1:
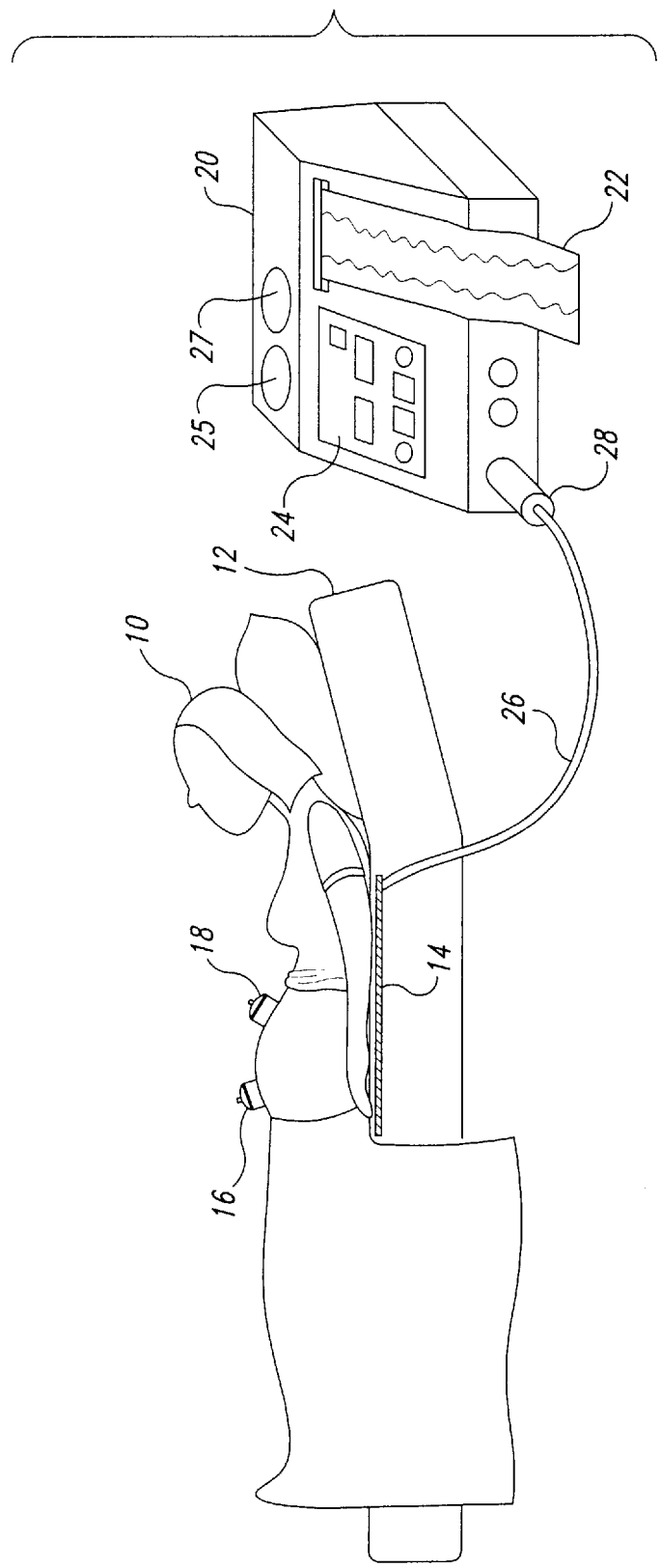
FIG. 1 is a diagram illustrating a wireless patient monitoring system in use in accordance with the present invention.

The wireless patient monitoring system of the present invention enables physiological functions to be monitored without the inconvenience of having multiple connecting cables attached between the transducers placed on the patient and the bedside monitoring instrumentation. FIG. 1 illustrates an example implementation of the invention, in which wireless fetal heart rate and maternal uterine monitoring is provided. A patient 10 is monitored while lying on bed 12. A mattress pad 14 is placed under the patient. An ultrasound transducer 16 is provided for monitoring fetal heart rate. A tocodynamometer transducer ("TOCO" or "TOCO transducer") 18 is provided for monitoring maternal uterine activity. Each of transducer assemblies 16 and 18 includes a transducer for providing an output signal indicative of the physiological function being monitored. Thus, in the case of transducer assembly 16, an ultrasound transducer provides an output signal indicative of fetal heart rate. The TOCO transducer assembly 18 includes a strain gauge or the like for providing an output signal indicative of uterine activity.

Both of the transducer assemblies include modulators for modulating a low frequency carrier by the respective output signal produced by the transducer within the transducer assembly. For purposes of the present disclosure, a "low frequency carrier" is defined as a carrier below the RF spectrum that can be coupled by electromagnetic induction. For example, the ultrasonic transducer incorporated in transducer assembly 16 can provide the transducer output signal on a carrier having a frequency of 8000 hertz, and the TOCO transducer can provide its output signal modulated on a 3100 hertz carrier. In the illustrated embodiments, FM modulation is used. However, it should be appreciated that other well known types of modulation, such as amplitude modulation (AM) could alternatively be used.

Each of the transducer assemblies 16, 18 includes a transducer coil associated with the respective modulator for coupling the modulated low frequency carrier to a corresponding receiver coil by electromagnetic induction. In the embodiment illustrated in FIG. 1, the receiver coil is located in mattress pad 14. The transducer assemblies 16, 18 are self-contained, battery operated units that do not require any external connections.

Each of the transducers 16, 18 radiates the received fetal/maternal signals via the low power frequency modulated magnetic field. The magnetic field is sensed by the mattress pad 14, which is connected via cable 26 and connector 28 to a receiver located in a bedside fetal monitoring console 20. The receiver within console 20 demodulates the magnetic field signals to provide ultrasound audio and uterine activity to a fetal monitor for conventional processing. Console 20 includes a control panel 24 having standard controls such as a digital display, audio volume controls, recorder controls, and the like. A strip chart recorder outputs strip documentation of patient data and monitored physiological functions on strip 22. Receptacles 25 and 27 are provided for charging batteries located in the transducer assemblies 16 and 18.

Figure 2:
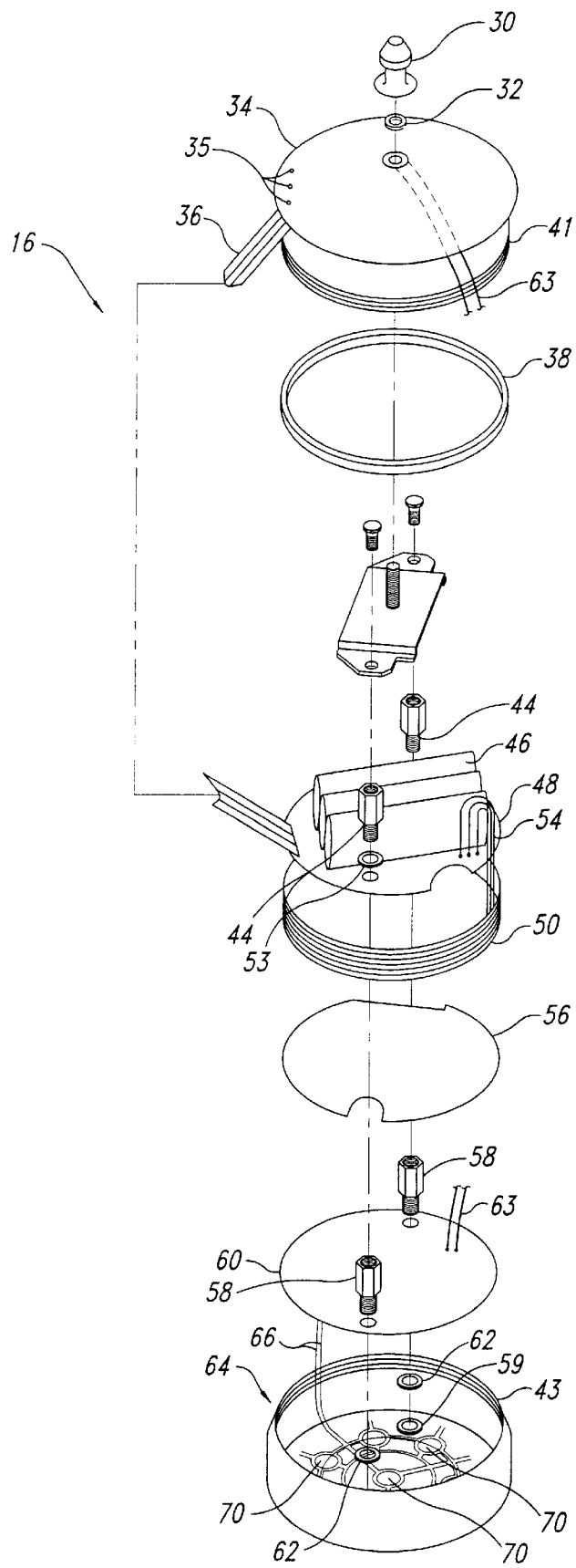
FIG. 2 is an exploded view of a wireless ultrasound transducer assembly.

FIG. 2 illustrates the ultrasound transducer assembly 16 in greater detail. A transducer knob 30 threadedly engages a threaded shaft 41 extending from bracket 42 in order to hold the unit into a closed, watertight assembly. Knob 30 can engage an opening in a strap (not shown) that straps the transducer assembly onto the patient. A washer 32 is provided between the knob 30 and top cover 34. A plurality of light emitting diodes (LEDs) 35 are provided in top cover 34 for indicating the condition of rechargeable (e.g., NiCad) batteries 46 within the assembly. Wires 36 couple the LEDs 35 to a power supply printed circuit board 48 ("battery board"). An "O" ring 38 seals top cover 34 against base assembly 64, so that the unit is watertight when assembled.

Bracket 42 is held to the base 64 via screws 40, threaded connectors 44 and threaded connectors 58. The threaded connectors 44 screw into threaded connectors 58, which in turn are screwed into threaded receptacles 59 of base 64. Insulating washers 53 and 62 are provided as shown.

Two coils 50 and 52 are provided within the transducer assembly. Coil 50 is a battery charging coil, which receives charging current inductively from either charging receptacle 25 or 27 of console 20 when the transducer assembly is inserted into the receptacle. This coil can be constructed, for example, from 36 turns of 30 gauge solid copper wire, with a coil diameter of about 2.5 inches. The coil has a center tap which is grounded. Coil 52 is the transducer coil which couples the transducer output signal to the receiver coil (e.g., in mattress pad 14) via electromagnetic induction. This coil can comprise 100–125 turns of 32 gauge solid copper wire, with a coil diameter of about 2.5 inches. A laminate Mylar/copper shield 56 is provided between the battery board 48 and an ultrasound transducer board 60, which contains circuitry for processing and modulating the ultrasound signals which are indicative of fetal heart rate. It should be understood that transducer board 60 is a printed circuit board containing various electronic components which are not specifically shown in the drawing.

In the embodiment illustrated in FIG. 2, seven ultrasonic transducer crystals 70 are mounted to the bottom of base 64. These crystals are coupled to the ultrasound transducer board 60 via wires 66.

Figure 3:
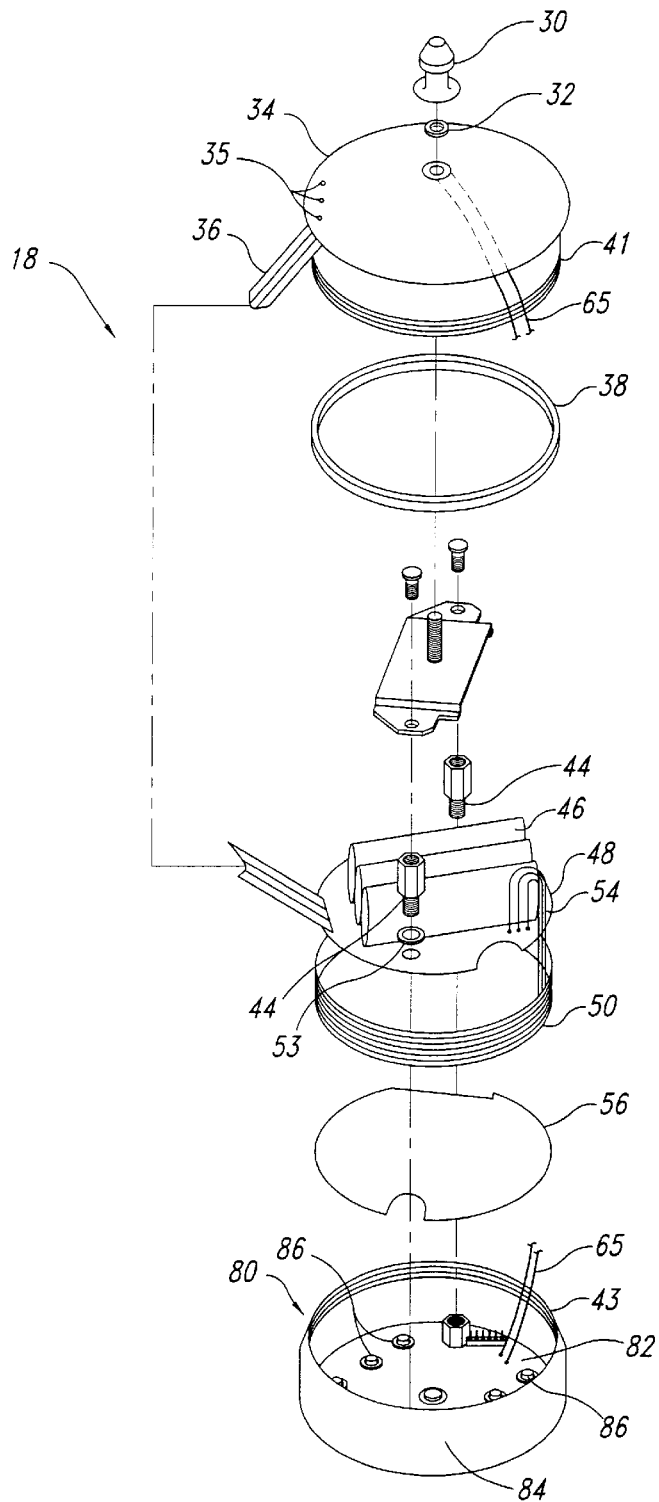
FIG. 3 is an exploded view of a wireless tocodynamometer transducer assembly.

FIG. 3 illustrates the TOCO transducer assembly 18 in greater detail. Parts which are identical with those of the ultrasound transducer bear the same reference numbers as in FIG. 2. The TOCO transducer differs from the ultrasound transducer in that instead of providing ultrasound printed circuit board 60, a TOCO transducer board 82 is provided. This PC board contains the circuitry required to process signals from a strain gauge 84 contained in the TOCO transducer base 80. The strain gauge is mounted to the TOCO transducer board 82 via fasteners 86, which can comprise small nuts and bolts. Wired TOCO transducers are well known in the art, and the assembly of the strain gauge within base 80 is conventional.

Figure 4:
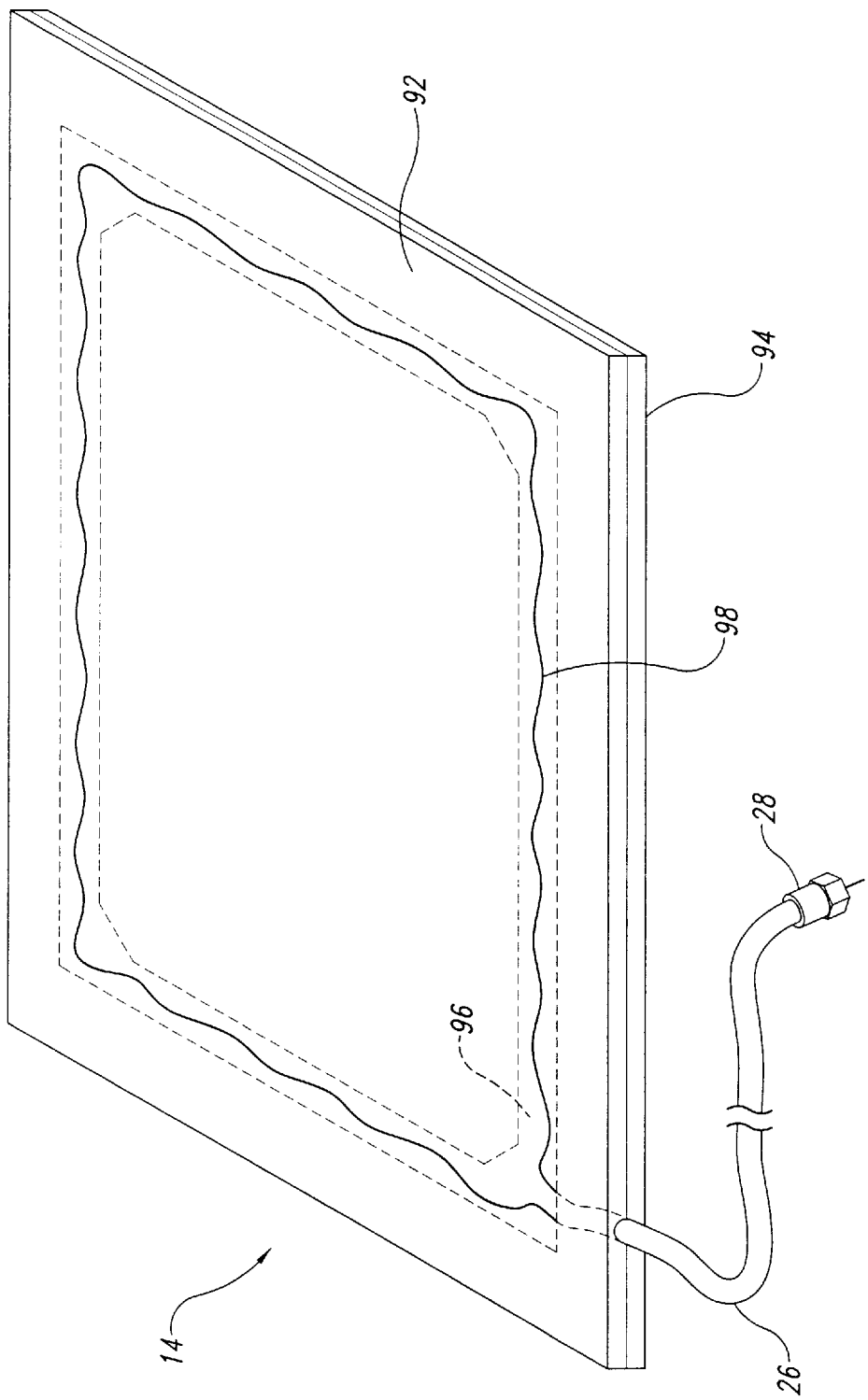
FIG. 4 is a diagram illustrating a mattress pad in accordance with the present invention.

The mattress pad 14 is illustrated in greater detail in FIG. 4. The mattress pad comprises two vinyl or other electrically nonconductive sheets 92, 94 which are fastened together using ultrasonic welding, a vinyl adhesive, or other well known technique. A channel 96 is provided within the mattress pad by providing a depression in the interior face of one or both of sheets 92 and 94. For example, the depression can be formed by abrasion after the sheet is manufactured or by heat and pressure during the manufacture of the sheet. Other techniques for forming a channel within the two adjoining sheets will be apparent to those skilled in the art.

A receiver coil 98 is placed within channel 96 of the mattress pad 14. Although the receiver coil is illustrated in FIG. 4 using a solid line, it should be understood that the coil is sandwiched between the two sheets 92, 94 within the channel 96 provided therein. The coil can be formed, for example, from ten windings of 26 gauge solid copper wire, which is periodically taped around the perimeter thereof. The coil is loosely positioned within the channel 96 so that it will not break when the mattress pad is folded.

Cable 26, which is preferably a coaxial cable, is attached to the ends of the coil 98. The outer shield of coax cable 26 is electrically connected to one end of the coil 98 and the inner conductor is electrically connected to the other end of coil 98. Cable 26 is terminated at the other end with a connector 28, which can comprise, for example, a standard coaxial cable connector. Connector 28 is adapted to be connected to a corresponding socket on monitor console 20 as illustrated in FIG. 1. A filtering capacitor (e.g., on the order of one microfarad) can be placed across the conductors of cable 26 at the connector 28 in order to filter out high frequency interference from fluorescent lights and other electrical devices.

Figure 5:
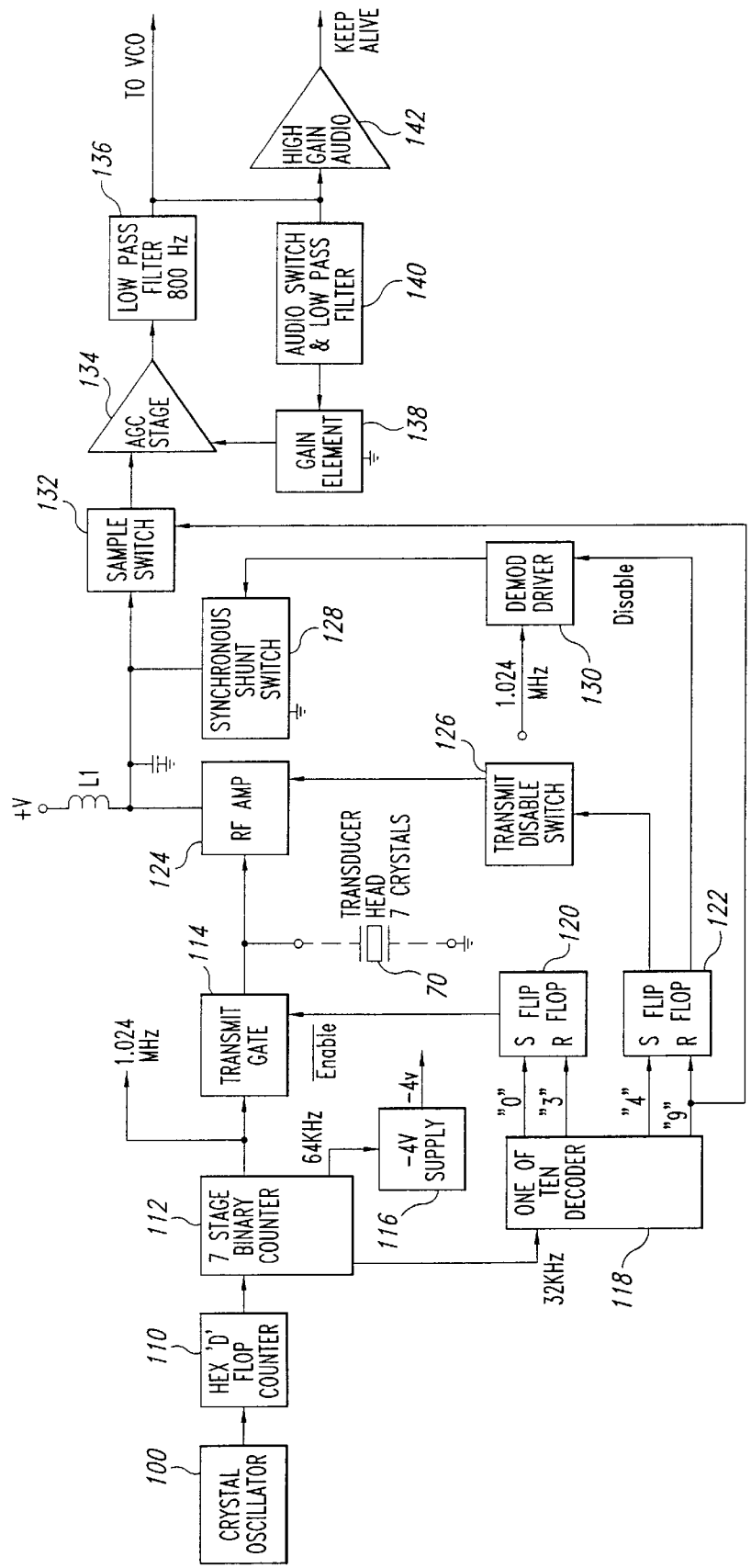
FIG. 5 is a block diagram illustrating circuitry incorporated into the ultrasound transducer of FIG. 2.

FIG. 5 is a block diagram of the ultrasound printed circuit board 60 illustrated in FIG. 2. The ultrasound transducer assembly contains a pulse Doppler transmitter and receiver. Such components are well known in the art. A crystal oscillator 100 (operating, e.g, at 6.144 MHz) feeds a HEX "D" flop counter 110, which divides the oscillator output by three to provide a 2.048 MHz output. A seven-stage binary counter 112 divides by two, to provide a 1.024 MHz output for driving the ultrasonic transducer crystals 70, through a transmit gate 114.

Counter 112 also supplies a 64 kHz output to a −4 volt supply 116 that is used to power various components on the ultrasound board. A 32 kHz output is provided from counter 112 to a one of ten decoder 118, which together with flip flops 120 and 122 and transmit disable switch 126 provide a desired pulse width for successive ultrasonic pulses and the waiting period therebetween. The 1.024 MHz output is directed from the transducer crystals to the fetal heart, and returns with a Doppler shift, such that the fetal heart sounds are detected over a range of about 50–300 hertz. An RF amplifier transistor 124 is used to amplify the output from the transducer crystals, in a conventional manner. A demodulator driver 130, which receives the 1.024 MHz signal, together with a synchronous shunt switch 128 are used to subtract out the 1.024 MHz input frequency from the Doppler shifted signal to provide the fetal heartbeat output in the 50–300 hertz range. A sample switch 132 avoids the need for complicated filtering, by taking short samples of the heart rate sounds at a high rate.

Figure 6:
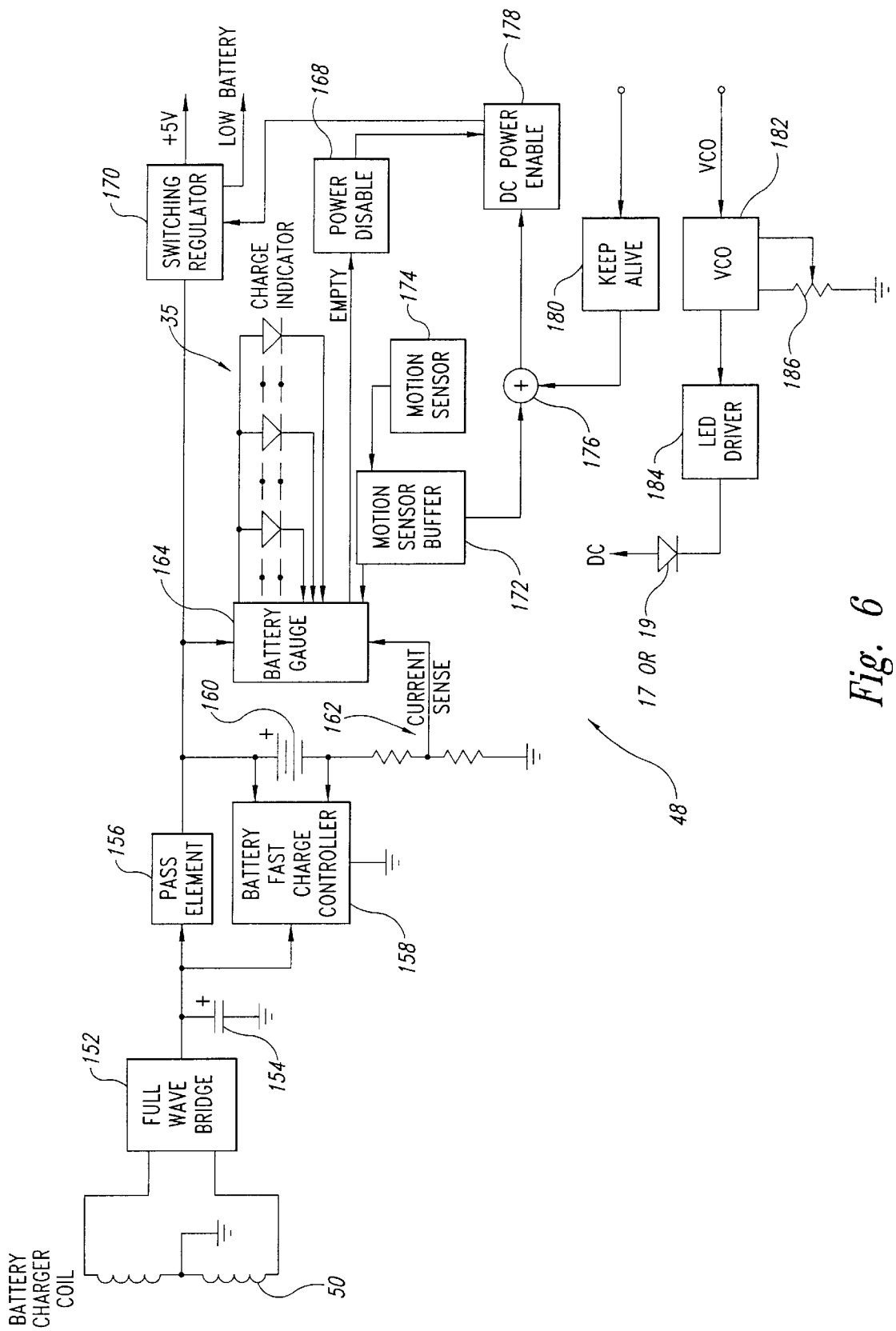
FIG. 6 is a block diagram illustrating power supply and oscillator circuitry found in the ultrasound transducer of FIG. 2 as well as the TOCO transducer of FIG. 3.

The samples output from switch 132 are input to an automatic gain control (AGC) loop containing an AGC stage 134, low pass filter 136, audio switch and low pass filter 140 and gain element 138. The AGC loop normalizes the amplitude of the audio before it is passed to the voltage controlled oscillator (VCO) that drives the transducer coil 52 (FIGS. 2 and 6). In this manner, the VCO can transmit a strong signal without overdriving the output. A high gain audio amplifier 142 is provided for use with a keep-alive circuit described below in connection with FIG. 6.

As indicated in FIG. 6, the audio output from low pass filter 136 of the ultrasound board (FIG. 5) is input to a VCO 182. The audio signal is used to frequency modulate a subcarrier produced by VCO 182, and the subcarrier is applied to the transmitter coil 52 via coil driver 184. As indicated above, the transmitter coil is mounted inside the perimeter of the ultrasound transducer housing. The coil driver 184 can simply comprise a transistor which outputs an FM modulated sine wave. Variable resistor 186 is provided in order to adjust the frequency of VCO 182. For the ultrasound transducer, the nominal output frequency of VCO 182 is, e.g., 8000 Hz and for the TOCO transducer, 3100 Hz. Other frequencies can, of course, be used as long as they are chosen such that they do not substantially interfere with each other.

Since the transmitter and receiver coils basically comprise a transformer, a null will occur when the transducer coil is oriented perpendicularly with respect to the receiver coil in the mattress pad. The range sensitivity is adjusted to reduce the null angle to a minimum. The operating range extends a few feet outside of the pad. In order to reduce or eliminate the null, it is possible for transmitter coil 52 to comprise a plurality of coils in different planes, e.g., perpendicular to each other. Instead of providing a plurality of transmitter coils in different planes, or in addition to such a structure, a plurality of receiver coils can be provided in different planes.

The battery board of FIG. 6 includes a battery charging circuit, a battery gauge, a motion sensor circuit for turning on power to the transducer assembly, and a keep-alive circuit for maintaining power when signals are being received. Essentially the same battery board is used with the ultrasound transducer and the TOCO transducer.

To facilitate ease of use and provide a waterproof transducer case, battery power is turned on via a motion sensing device. A motion sensor 174, which can comprise any type of switch that is activated by motion, provides an input to a motion sensor buffer 172. Examples of such switches include mercury switches and spring loaded mechanical switches that close a contact in response to any small motion. Upon a transition of the motion sensor contacts, an output signal generated by motion sensor buffer 172 is applied to an OR gate 176, the output of which activates a DC power enable circuit 178. In response, switching regulator 170 outputs power from battery pack 160.

After the transducer is placed onto a patient, a keep-alive circuit 180 senses the fetal heartbeat (ultrasound transducer) or uterine activity (TOCO transducer) and keeps the power on. The output of the keep-alive circuit is input to OR gate 176 to actuate DC power enable 178, which in turn actuates switching regulator 170 to output the battery power. The power remains on for a number of minutes after the transducer is removed from the patient, by virtue of a timer in DC power enable circuit 178.

Each transducer is powered by an internal rechargeable battery pack 160. Recharging is accomplished by placing the entire transducer into a receptacle 25 or 27 provided on the fetal monitor console (FIG. 1). The charging station contains a coil for inductively charging the battery pack via battery charger coil 50. The current received from the charging station is passed through a full wave bridge rectifier 152 and filtered by capacitor 154. A pass element 156, which can comprise a simple transistor, passes the charging current on to the rechargeable battery pack 160. A fast charge battery controller 158, which is an off-the-shelf integrated circuit, terminates the charge current by either detecting full battery capacity or detecting that a maximum allowable charge time has elapsed. Once the battery is fully charged, a trickle charge is maintained to keep the battery at full capacity.

Battery current is sensed via a voltage divider 162 for input to a battery monitoring circuit ("battery gauge") 164. This integrated circuit keeps track of battery usage and charge currents. Compensation is made for diminished battery capacity due to age and self-discharge. Each time a complete charge/discharge cycle is performed, the programmed full capacity is updated.

Three LED indicators 35 show the approximate remaining battery charge. The LED indicators are illuminated for a brief time period after each detected motion, at the end of battery life, and when the transducer is placed into the charging station. When the battery is near the end of its useful charge, at least one of the LED indicators will flash and a signal is transmitted to the fetal monitor console to notify the operator.

When the battery is discharged, a power disable circuit 168 responsive to the battery gauge actuates the DC power enable circuit 178 to turn off the switching regulator 170, thereby terminating the supply of power to the rest of the transducer circuitry. When the battery is low, the switching regulator outputs a "low battery" signal which, in the case of the ultrasound transducer, can be used to slightly shift the VCO frequency via the variable frequency adjusting resistance 186. Upon detecting a shifted ultrasound carrier, the receiver in the fetal monitor console will actuate a suitable low battery indicator.

Figure 7:
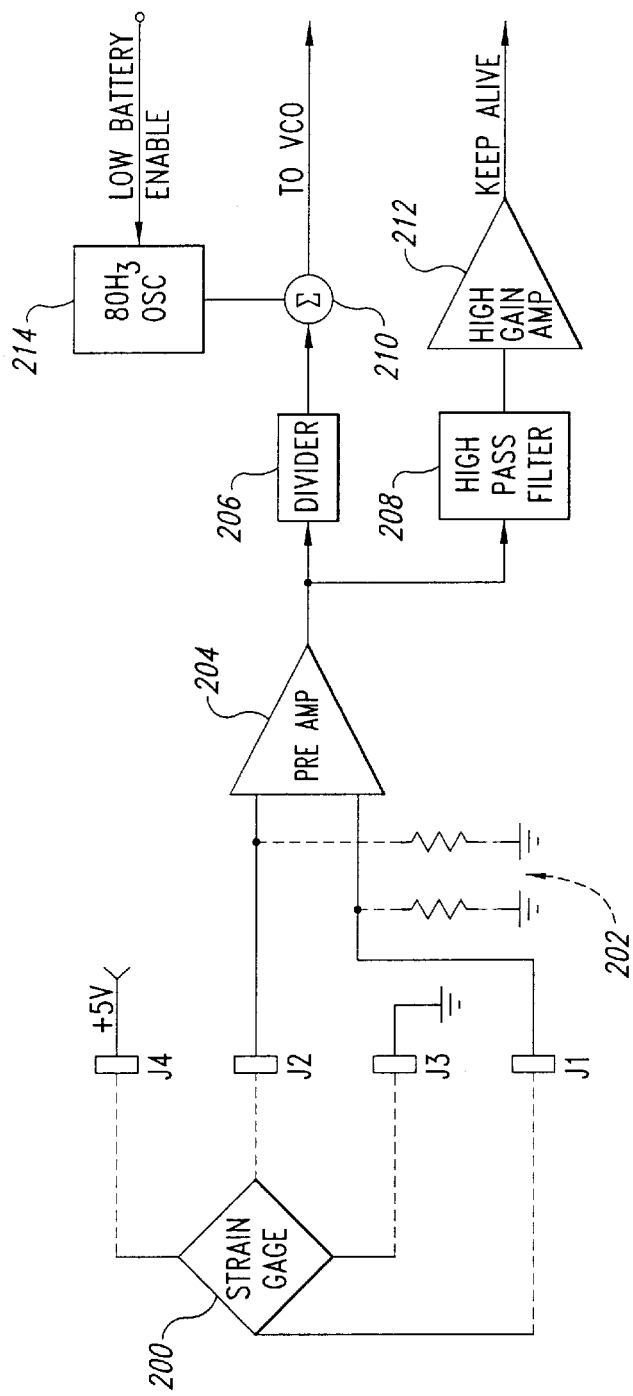
FIG. 7 is a block diagram of TOCO transducer circuitry found in the transducer of FIG. 3.

In the case of the TOCO transducer, the low battery signal from switching regular 170 is input to actuate to an oscillator 214 as illustrated in FIG. 7. The oscillator output (e.g., 80 Hz) is summed with the output carrier which carries the TOCO transducer signal for detection by the receiver circuitry in the fetal monitor console.

FIG. 7 illustrates the circuitry contained on the TOCO transducer printed circuit board 82 of FIG. 3. A strain gauge 200 detects uterine activity and produces an output signal that is amplified in preamplifier 204. Optional offset adjusting resistors 202 are provided to balance the strain gauge outputs.

The amplified output from the strain gauge is scaled in a divider 206, and summed with the output of oscillator 214 (when present). The resultant signal is output to the VCO 182 of a corresponding battery board 48 illustrated in FIGS. 3 and 6. As indicated above in connection with the ultrasound transducer, the strain gauge output of the TOCO transducer will FM modulate the VCO on the battery board of the TOCO transducer assembly, for output to a coil driver 184 and transmit coil 52.

The output of preamplifier 204 (FIG. 7) is also passed through a high pass filter 208 and a high gain amplifier 212 to provide a keep-alive signal that is input to the corresponding keep-alive circuit 180 on the TOCO transducer battery board. In this manner, once power to the TOCO transducer assembly is provided, it will remain as long as uterine activity is detected by the strain gauge, and for some predetermined time thereafter.

Figure 8:
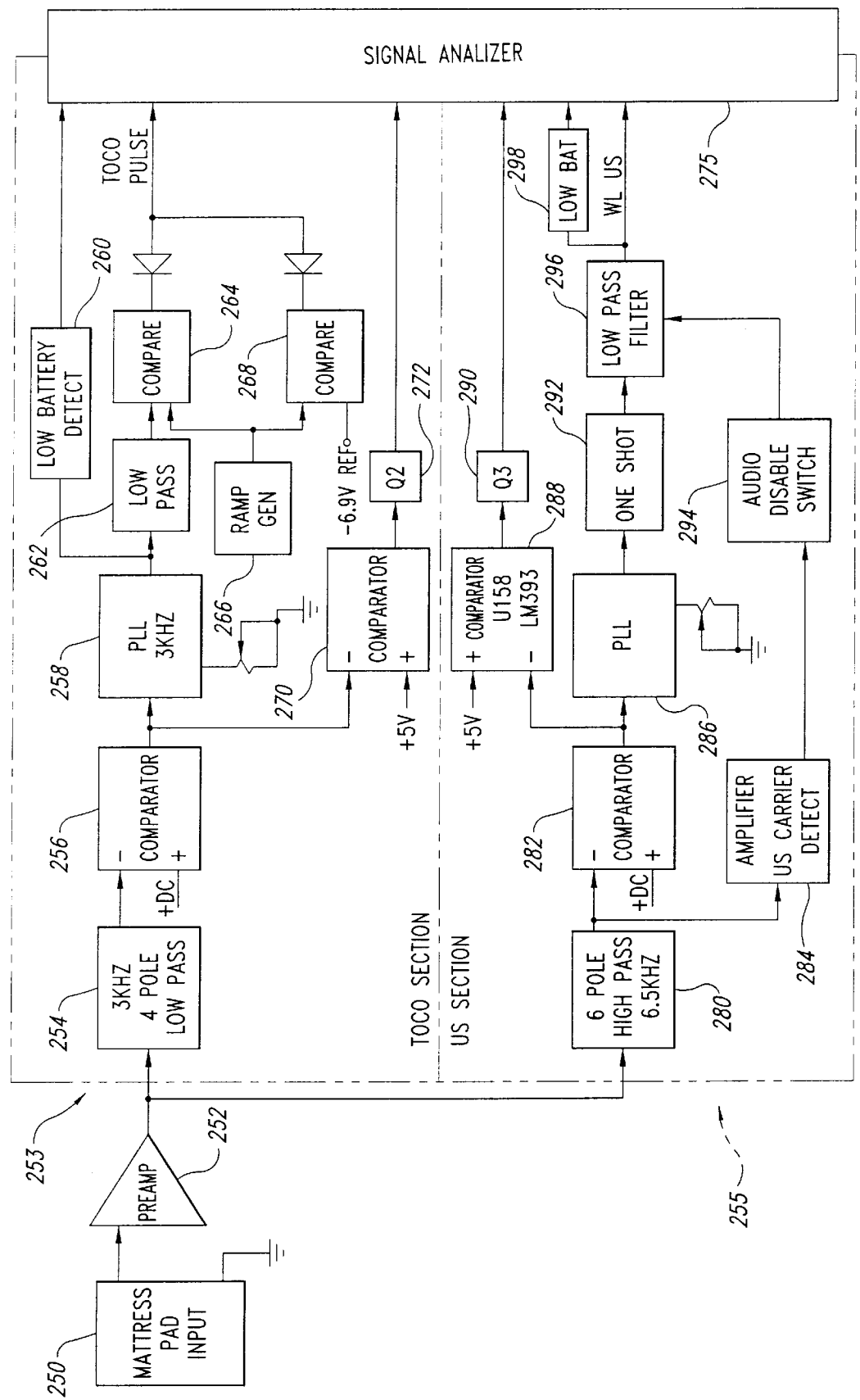
FIG. 8 is a block diagram illustrating a receiver for signals output from the ultrasound transducer of FIG. 2 and the TOCO transducer of FIG. 3.

FIG. 8 illustrates the receiver circuitry for processing the ultrasound and TOCO signals in the fetal monitor console. The signals coupled to the mattress pad are input to a preamplifier 252 via the mattress pad input 250. Preferably, the TOCO and ultrasound carrier frequencies will be chosen to be noninterfering with each other or with other signals such as the pulse Doppler repetition frequency. It has been found that an ultrasound carrier frequency of 8000 hertz and TOCO transducer carrier frequency of 3100 hertz is satisfactory.

The output of preamplifier 252 is input to a TOCO transducer processing circuit generally designated 253 and to ultrasound transducer processing circuitry generally designated 255. In the TOCO transducer section, the signal is received by a low pass filter 254 which passes the 3100 hertz TOCO carrier to a comparator 256. The comparator compares the TOCO carrier to a DC level and outputs a square wave to a phase-lock-loop (PLL) circuit 258 which locks onto the input frequency. The output of the PLL is a representation of TOCO pressure. This signal is low pass filtered by filter 262 and converted to a digital signal by comparators 264 and 268 which also receive an input from ramp generator 266. As indicated in FIG. 8, comparator 264 compares the TOCO signal to the ramp generator output. Comparator 268 compares the ramp generator output to a reference voltage. The combined output of the comparators is a pulse width modulated signal representative of uterine activity, which is input to a conventional microprocessor controlled signal analyzer 275 in the fetal monitor console.

A comparator 270 is provided in the TOCO section of the receiver for detecting the presence of a wireless TOCO signal. If no wireless signal is present (i.e., no modulated low frequency TOCO carrier is detected), a transistor 272 will output a signal to signal analyzer 275 in order to switch the fetal monitor to a cable mode of operation. In the cable mode, the fetal monitor uses conventional wired transducer assemblies.

The ultrasound section of the receiver includes a high pass filter 280 that recovers the ultrasound transducer carrier from the signal output by preamplifier 252. After processing by a comparator 282 and phase-lock-loop 286, the signal is demodulated using a monostable multivibrator (one-shot) 292 and low pass filter 296. The demodulated audio is then provided to the conventional signal analyzer 275.

Amplifier 284 detects the level of the ultrasound carrier. If the level is too weak, amplifier 284 actuates an audio disable switch 284 to mute the audio via low pass filter 296. A comparator 288 and transistor 290, analogous to comparator 270 and transistor 272 of the TOCO receiver circuitry, switch the fetal monitor to the cable mode of operation when no wireless ultrasound signal is present.

Both the TOCO section 253 and ultrasound section 255 are provided with respective low battery detection circuits 260, 298. The TOCO section low battery detection circuit 260 detects the 80 hertz signal added to the TOCO transducer output via oscillator 214, discussed above in connection with FIG. 7. The ultrasound low battery detector 298 detects a frequency shift introduced via the VCO 182 in the ultrasound transducer assembly when the battery power is low, as discussed above in connection with FIG. 6. The detection of a low battery signal in either the TOCO transducer or the ultrasound transducer will result in a notification signal being generated in signal analyzer 275.

It should now be appreciated that the present invention provides a wireless patient monitoring apparatus in which low frequency inductive coupling is used to communicate signals from self-contained, portable transducer assemblies to patient monitoring apparatus. The signals are coupled from a transmitter coil in the transducer assembly to a receiver coil, which can be provided, for example, in a mattress pad. The use of low frequency inductive coupling avoids the drawbacks of prior art radio frequency telemetry systems, such as interference with other instrumentation.

Although the invention has been described in connection with a preferred embodiment, it should be appreciated that various adaptations and modifications may be made thereto without departing from the spirit and scope of the invention as set forth in the claims.

We claim:

1. Wireless patient monitoring apparatus comprising:
   a transducer configured to detect a physiological function and to provide an output signal indicative of the physiological function;
   a modulator configured to modulate a carrier having a frequency at or below 10 kHz by the output signal;
   a transducer coil associated with said modulator for coupling the modulated carrier to a corresponding receiver coil by electromagnetic induction; and
   a monitoring circuit coupled to receive the modulated carrier from the receiver coil;
   wherein said transducer is designed for placement adjacent to a region of a patient to be monitored and provides the output signal to said monitoring circuit when the patient is in proximity to the receiver coil.

2. Apparatus in accordance with claim 1 wherein said transducer, modulator and transducer coil are all situated in a common transducer housing.

3. Apparatus in accordance with claim 2 further comprising:
   a power supply in said housing for powering said transducer, said modulator, and associated circuitry situated in the housing; and
   a motion sensor situated in said housing for detecting movement of the housing;
   wherein said power supply is responsive to said motion sensor for providing power when the housing is moved.

4. Apparatus in accordance with claim 3 further comprising:
   a keep-alive circuit for actuating said power supply to continue to provide power when said physiological function is being detected.

5. Apparatus in accordance with claim 2 wherein said housing is a waterproof housing.

6. Apparatus in accordance with claim 2 wherein said receiver coil is situated in a mattress pad.

7. Apparatus in accordance with claim 1 wherein said receiver coil is situated in a mattress pad.

8. Apparatus in accordance with claim 7 wherein a plurality of receiver coils are provided in different planes of said mattress pad.

9. Apparatus in accordance with claim 1 wherein a plurality of receiver coils are provided in different planes.

10. Apparatus in accordance with claim 1 wherein a plurality of transducer coils are provided in different planes.

11. Apparatus in accordance with claim 1 wherein said transducer comprises an ultrasound transducer adapted to be placed on a mother's abdomen and said physiological function comprises fetal heart rate.

12. Apparatus in accordance with claim 11 wherein said receiver coil is situated in a mattress pad.

13. Apparatus in accordance with claim 12 further comprising a tocodynamometer transducer adapted to be placed on the abdomen for providing a TOCO output signal indicative of uterine activity, said tocodynamometer transducer comprising:
   a TOCO modulator configured to modulate a TOCO carrier having a frequency at or below 10 kHz by the TOCO output signal; and
   a TOCO transducer coil associated with said TOCO modulator configured to couple the TOCO carrier to the receiver coil by electromagnetic induction;
   wherein said TOCO transducer is adapted to provide said TOCO output signal to a monitoring circuit via said TOCO transducer coil and the receiver coil when the mother is in proximity to the receiver coil.

14. Apparatus in accordance with claim 13 wherein said receiver coil is situated in a mattress pad.

15. Apparatus in accordance with claim 13 wherein the output signals from said ultrasound and tocodynamometer transducers are modulated on separate subcarriers for inductive coupling to said receiver coil.

16. Apparatus in accordance with claim 1 wherein said transducer, modulator and transducer coil are all situated in a common transducer housing, said apparatus further comprising:
   a battery operated power supply in said housing for powering said transducer, said modulator, and associated circuitry situated in the housing; and
   a first charging coil in said housing for use in inductively charging said batteries.

17. Apparatus in accordance with claim 16 further comprising:
   a console containing said monitoring circuit;
   a receptacle in said console for removably receiving said transducer housing; and a second charging coil, located adjacent to said receptacle, for inductively providing a charging current to the first charging coil when the transducer housing is placed in said receptacle.

18. Apparatus in accordance with claim 16 further comprising:

means for communicating a low battery signal to an external indicator via said transducer and receiver coils.

19. A method for monitoring on a patient, comprising:

detecting a physiological function of a patient;

generating an output signal indicative of the physiological function;

radiating the output signal via a magnetic field oscillating at a frequency at or below 10 kHz;

detecting the magnetic field indicative of the physiological function; and recovering the output signal from the magnetic field to monitor the physiological function.

20. The method of claim 19, further comprising ultrasonically detecting a physiological function of a patient.

21. The method of claim 19, further comprising tocodynamometrically detecting a physiological function of a patient.

22. The method of claim 19, further comprising detecting a fetal heart rate of a patient.

23. The method of claim 19, further comprising detecting a uterine activity of a patient.

24. An inductive patient monitoring device, comprising:

means for detecting a physiological function;

means for providing an output signal indicative of the physiological function;

means for radiating the output signal via a magnetic field oscillating at a frequency at or below 10 kHz;

means for receiving the output signal via the magnetic field; and means for recovering the output signal from the magnetic field to monitor the physiological function.

25. The device of claim 24, further comprising means for detecting a fetal heart rate or means for detecting a uterine activity of the patient being monitored using the transducer.

26. The apparatus of claim 1 wherein the receiver coil is shaped in a loop and wherein the transducer coil is positioned within the confines of the receiver coil loop.

27. A monitoring apparatus adapted to monitor a physiological function of a patient positioned on a bed, the apparatus comprising;

a mattress pad positioned on a mattress, the mattress pad having a receiver loop;

a transducer configured to detect a physiological function of a patient, the transducer being operable to provide an output signal indicative of the physiological function;

a modulator coupled to the transducer and being configured to modulate a carrier having a frequency at or below 10 kHz by the output signal;

a transducer coil coupled to the modulator configured to radiate the modulated carrier by a magnetic field, the transducer coil being positioned within the periphery of the receiver loop; and a monitoring circuit coupled to receive the modulated carrier from the receiver loop.

* * * * *